United States Patent [19]
Hayes et al.

[11] Patent Number: 6,031,148
[45] Date of Patent: Feb. 29, 2000

[54] IMPLANTABLE BIOABSORBABLE ARTICLE

[75] Inventors: Byron Kent Hayes; William R. Hardwick, both of Flagstaff; Charles F. White, Camp Verde; Mark D. Butler, Flagstaff, all of Ariz.

[73] Assignee: W. L. Gore & Associates, Inc., Newark, Del.

[21] Appl. No.: 08/042,293

[22] Filed: Apr. 2, 1993

Related U.S. Application Data

[62] Division of application No. 07/622,869, Dec. 6, 1990, abandoned.

[51] Int. Cl.[7] .............................. A61F 2/02; A61F 2/06; A61F 2/04; A61B 17/08
[52] U.S. Cl. .................. 623/11; 623/1; 623/12; 606/152; 606/154; 600/37
[58] Field of Search .................... 606/152, 154; 623/1, 11, 12; 600/37

[56] References Cited

U.S. PATENT DOCUMENTS

| | | |
|---|---|---|
| 2,748,781 | 6/1956 | Collat . |
| 2,991,224 | 7/1961 | Bell . |
| 3,386,440 | 6/1968 | Cohen . |
| 3,589,011 | 6/1971 | Sneer . |
| 3,754,332 | 8/1973 | Warren, Jr. . |
| 3,855,638 | 12/1974 | Pilliar . |
| 3,863,344 | 2/1975 | Pillet . |
| 3,879,767 | 4/1975 | Stubstad . |
| 3,909,852 | 10/1975 | Homsy . |
| 3,953,566 | 4/1976 | Gore . |

(List continued on next page.)

FOREIGN PATENT DOCUMENTS

| | | |
|---|---|---|
| 0 089 782 | 9/1983 | European Pat. Off. . |
| 0 171 173 | 2/1986 | European Pat. Off. . |
| 0 274 898 | 7/1988 | European Pat. Off. . |
| 0 303 496 | 2/1989 | European Pat. Off. . |
| 0359575 | 3/1990 | European Pat. Off. . |
| 0370292 | 5/1990 | European Pat. Off. . |
| 1 499 912 | 3/1967 | France . |
| 2 306 672 | 5/1976 | France . |
| 2 635 966 | 3/1990 | France . |
| 0560934 | 8/1996 | France . |

(List continued on next page.)

OTHER PUBLICATIONS

John F. Richard, D.D.S., "Criteria for Verifying Topographical Changes in Aleveolar Process After Surgical Intervention", Periodontics, vol. 4, No. 2, pp. 71–76 (Mar./Apr. 1966).

John F. Richard, "The Diagnosis and Management of Vertical Bony Defects", Periodontols, vol. 54, No. 1, pp. 29–35 (Apr. 1982).

Birgit Ellegaard et al., "New Periodontal Attachment Procedure Based on Retardation of Epithellial Migration", Journal of Clinical Peridontology, vol. 1, pp. 75–88 (1974).

I. Aukhill et al., "An Experimental Study of New Attachment Procedure in Beagle Dogs", Journal of Peridontal Research, vol. 18, pp. 643–654 (1983).

Jacob Shiloah, "The Clinical Effects of Citric Acid and Laterally Positioned Pedicle Grafts in the Treatment of Denuded Root Surfaces", Journal of Peridonol, vol. 51, No. 11, pp. 652–654 (1980).

(List continued on next page.)

*Primary Examiner*—John G. Weiss
*Assistant Examiner*—K. M. Reichle
*Attorney, Agent, or Firm*—Wayne D House

[57] ABSTRACT

An implantable bioabsorbable article for the separation and regeneration of tissue at a tissue defect site in the form of a fibrous matrix laminarly affixed to both surfaces of a cell-barrier sheet material. When implanted it allows ingrowth of tissue into the fibrous matrix side of the material; simultaneously the tissue to be regenerated at the tissue defect site is separated from the ingrowing tissue by the cell-barrier sheet material. A method for making the implantable bioabsorbable article is also described.

21 Claims, 13 Drawing Sheets

U.S. PATENT DOCUMENTS

| | | |
|---|---|---|
| 3,971,134 | 7/1976 | Bokros . |
| 3,971,670 | 7/1976 | Homsy . |
| 4,007,494 | 2/1977 | Sauer . |
| 4,020,558 | 5/1977 | Cournut et al. . |
| 4,039,653 | 8/1977 | DeFoney et al. . |
| 4,136,162 | 1/1979 | Fuchs et al. . |
| 4,175,326 | 11/1979 | Goodson . |
| 4,187,390 | 2/1980 | Gore . |
| 4,195,405 | 4/1980 | Child . |
| 4,244,689 | 1/1981 | Ashman . |
| 4,252,525 | 2/1981 | Child . |
| 4,303,712 | 12/1981 | Woodruff . |
| 4,321,914 | 3/1982 | Begovac et al. . |
| 4,400,833 | 8/1983 | Kurland . |
| 4,492,577 | 1/1985 | Farris et al. . |
| 4,520,821 | 6/1985 | Schmidt et al. . |
| 4,531,916 | 7/1985 | Scantlebury et al. . |
| 4,534,349 | 8/1985 | Barrows . |
| 4,595,713 | 6/1986 | St. John . |
| 4,643,734 | 2/1987 | Lin ............................................ 623/16 |
| 4,655,777 | 4/1987 | Dunn et al. . |
| 4,664,474 | 5/1987 | Barrows . |
| 4,743,252 | 5/1988 | Martin, Jr. et al. ......................... 623/1 |
| 4,752,294 | 6/1988 | Lundgren . |
| 4,841,962 | 6/1989 | Berg et al. . |
| 4,870,966 | 10/1989 | Dellon et al. . |
| 4,883,618 | 11/1989 | Barrows . |
| 4,886,870 | 12/1989 | D'Amore et al. . |
| 4,916,193 | 4/1990 | Tang et al. ............................... 608/154 |
| 4,923,470 | 5/1990 | Dumican . |
| 4,961,707 | 10/1990 | Magnusson et al. . |
| 5,010,009 | 4/1991 | Steele et al. . |
| 5,011,486 | 4/1991 | Aebischer et al. ....................... 606/152 |
| 5,024,671 | 6/1991 | Tu et al. ....................................... 23/1 |
| 5,032,445 | 7/1991 | Scantlebury et al. . |
| 5,061,281 | 10/1991 | Mares et al. . |
| 5,077,049 | 12/1991 | Dunn et al. . |
| 5,084,051 | 1/1992 | Törmälä et al. .......................... 623/13 |
| 5,651,505 | 7/1997 | Bowald et al. . |
| 5,676,699 | 10/1997 | Gogolewski et al. . |

FOREIGN PATENT DOCUMENTS

| | | |
|---|---|---|
| 3830481 | 3/1990 | Germany . |
| 1 390 445 | 4/1980 | United Kingdom . |
| 1 602 932 | 11/1981 | United Kingdom . |
| 2 161 080 | 1/1986 | United Kingdom . |
| 2 222 954 | 3/1990 | United Kingdom . |
| 2222954 | 3/1990 | United Kingdom . |
| 8 600 517 | 1/1986 | WIPO . |
| 9 001 824 | 1/1986 | WIPO . |
| 8 805 312 | 7/1988 | WIPO . |
| 90/00410 | 1/1990 | WIPO . |
| WO90/07308 | 7/1990 | WIPO . |
| 9 011 730 | 10/1990 | WIPO . |
| 9 013 302 | 11/1990 | WIPO . |

OTHER PUBLICATIONS

Barry L. Radall et al. "A Clinical Evaluation of Proplast as a Periodontal Implant Material", Journal of Periodontol, vol. 51, No. 2, pp. 110–115 (1980).

Opposition to EP 0560934 on behalf of Ethicon GmbH & Co., May 5, 1997.

Opposition to EP 0560934 on behalf of Biocon OY.

Pfeifer et al., "Epithelial Exclusion and Tissue Regeneration Using A Collagen Membrane Barrier . . . ", Int. J. Perio. Rest. Dent., 1989, vol. 9, pp. 263–273.

Vicryl Periodontal Mesh, Use Manual.

Wikesjo et al., "Periodontal Repair in Dogs: Effect of Saliva Contamination Of The Root Surface", J. Periodontal, 1990, vol. 61, pp. 559–563.

Gottlow et al., "New Attachment Formation In The Human Periodontium . . . ", Journal of Clin. Periodontology, 1986, vol. 13, pp. 604–616.

Lewis, "Controlled Release of Bioactive Agents From Lactide/Glycolide Polymers", pp. 1–41; Biodegradable Polymers As Drug Delivery Systems, 1990.

Magnusson et al., "New Attachment Formation Following Controlled Tissue . . . " J. Periodontal, 1988, vol. 59, pp. 1–6.

Fleisher et al., "Regeneration of Lost Attachment Apparatus In The Dog Using Vicryl Absorbable Mesh", International Journal of Perio. & Rest. Dent., Feb. 1988, pp. 45–55.

Gore–Tex, Guided Tissue Regeration Workshop Manual.

Gore–Tex®, Augmentation Material Preliminary Procedural Guidelines And Order Information.

Caffesse et al., "New Attachment Achieved By Guided Tissue Regeneration In Beagle Dogs," J. Periodontal, 1988, vol. 59, pp. 589–594.

Claffey et al., "Effect of Placement of Occlusive Membranes on Root Resorption And Bone Regeneration . . . ", J. Clin. Periodontal, 1989, vol. 16, pp. 371–379.

Aukhil et al., "Guided Tissue Regeneration", J. Periodontal, vol. 57, No. 12, pp. 727–734 (1986).

Prichard, "The Roentgenographic Depiction of Periodontal Disease", J. Clin. Periodontal, vol. 11:494 (1984).

Langer et al., "Chemical and Physical Structure of Structure of Polymers as Carriers for Controlled Release of Bioactive Agents: A Review", 4022 J. of Macromolecular Science Reviews on Macromolecular Chemistry and Physics C23 (1983), No. 1.

Murray et al., "Experimental and Clinical Study of New Growth of Bone in a Cavity", American J. of Surgery, vol. 93, Mar. (1957).

Linghorne, "The Sequence of Events in Osteogenesis As Studied in Polyethylene Tubes", Annals New York Academy of Sciences 85:455–460 1960.

Melcher et al., "Protection of the Blood Clot in Healing Circumscribed Bone Defects", J. of Bone and Joint Surgery, vol. 44B, No. 2, pp. 424–430 (1962).

Gongloff et al., "Use of Collagen Tubes for Implantation of Hydroxyl–apatite", J. of Maxillofacial Surgery 43:570–573 (1985).

Dahlin et al., "Healing of Bone Defects by Guided Tissue Regeneration", Surgery,vol. 81, No. 5, pp. 672–676 (1988).

Magnusson et al., "Connective Tissue Attachment Formation Following Exclusion of Gingival Connective Tissue and Epithelium During Healing", J. of Periodontal Research, vol. 20, pp. 201–208, (1985).

Pitaru et al., "Partial Regeneration of Periodontal Tissue Using Collagen Barriers", J. Peridontal, vol. 59, No. 6, pp. 380–386 (1988).

Velasco et al., "A Study of Autologous Cancellous Bone Particles in Long Bone Discontinuity Defects", Clinical Orthopaedics and Related Research, No. 177, pp. 264–273 (1983).

H.A. Zander et al., "Goals of Periodontal Therapy", J. Periodontal 47:261, 1976.

A. H. Melcher et al., "On the Repair Potential of Periodontal Tissues", J. Periodontal 47:256, 1976.

McCulloch et al., "Cell Density and Cell Generation in the Periodontal Ligament of Mice", Am. J. Anat., 167:43, 1983.

Aukil et al., "Periodontal Wound Healing in the Absence of Periodontal Ligament Cells", J. Peridontal 58:71, 1987.

Nyman et al., "The Regenerative Potential of the Periodontal Ligament, An Experimental Study in the Monkey", J. Clin. Periodontal 9:257, 1982.

Gottlow et al., "New Attachment Formation as the Result of Controlled Tissue Regeneration", J. Clin. Peridontal 11:494, 1984.

Caton et al., "Periodontal Regeneration Via Selective Cell Repopulation", J. Periodontal 58:546, 1987.

Quiones et al., "Evaluation of a Synthetic Biodegradable Barrier to Facilitate Guided Tissue Regeneration", J. Dent. Res. 69: Special Issue, 1990, Abstract No. 1336.

Caton et al., "Synthetic Biodegradable Barrier for Regeneration in Human Periodontal Defects", J. Dent. Res. 69: Special Issue, 1990, Abstract No. 1335.

IMPLANTABLE BIOABSORBABLE ARTICLE

CROSS-REFERENCE TO RELATED APPLICATIONS

This application is a division of U.S. application Ser. No. 07/622,869, filed Dec. 6, 1990, now abandoned.

FIELD OF THE INVENTION

This invention relates to an implantable bioabsorbable article for use as a mammalian-cell-barrier to aid in the regeneration of tissue.

BACKGROUND OF THE INVENTION

A preferred technique to promote the regeneration of mammalian tissue is accomplished by the separation and isolation of a particular type of tissue to be regenerated from other competing undesirable tissues through the use of a biocompatible barrier material. This concept is known as guided tissue regeneration and was described in an article by J. Gottlow, et al., titled "New Attachment Formation in the Human Periodontium by Guided Tissue Regeneration" (Journal of Clinical Periodontology, 1986; Vol. 13, pp. 604–616). The function of the barrier material is to substantially preclude the movement of tissue cells through the thickness of the material and consequently limit the varieties of cell types at the treatment site. This function is combined with the requirement that the material maintain sufficient space adjacent to the defect so as to allow for the regeneration of the desirable tissue into that space. The preservation of space between the surface of the defect and the desired contours of the subsequently regenerated surface is necessary in order to allow for the regeneration of tissues into that space. Specific periodontal structures which may be regenerated in this fashion are the periodontal ligament, bone and cementum. The barrier material allows propagation of bone and periodontal ligament cells by precluding epithelial cells and gingival connective tissue cells which are believed to propagate at a greater rate. This concept may be useful for other applications where separation of specific cell varieties is desirable such as, for example, nerve repair and nerve guidance applications, bone regeneration and prevention of soft tissue adhesions, particularly those of the peritoneum.

A description of a bioabsorbable tubular device useful for nerve repair is provided in U.S. Pat. No. 4,870,966 to Dellon, et al.

Additionally, it has been proposed that the mechanical stability of the blood clot which forms in the defect space adjacent to the tooth root after periodontal surgery may be important to the regeneration process (Wikesjo et al., 1990; J. Periodontal., Vol. 61, 559–563). Therefore a material which can become infiltrated with blood clot and thus form a connection between the material and the adjacent gingival flap may add to the mechanical stability of the wound.

One commercially available material that provides a cell-barrier for periodontal tissue regeneration is the GORE-TEX Periodontal Material. This polytetrafluoroethylene (PTFE) material serves as a cell-barrier between the gingiva and a periodontal defect and is intended to preserve necessary space between the surface of the defect and the desired contours of the subsequently regenerated surface. The GORE-TEX Periodontal Material is made of porous expanded PTFE having a microstructure of nodes interconnected by fine fibrils. This commercially available material is not of laminar construction and its porosity is generally uniform through the thickness of the material. One portion of the total surface area of the GORE-TEX Periodontal Material has a porous structural surface that becomes infiltrated with blood clot and ingrown with fibrous connective tissue, thereby inhibiting epithelial migration. The remaining portion of the surface area has a cell-barrier structure of low porosity for isolating the overlying gingival connective tissue from the underlying defect. It is not bioabsorbable and is typically removed in a subsequent surgical procedure.

There have been previous attempts to produce suitable surgical barriers from bioabsorbable materials. A 70 micron thick membrane solvent-cast from bioabsorbable polylactic acid, having no inherent porosity or tissue cell permeability, was tested in periodontal applications as a cell-barrier material for exclusion of epithelium and gingival connective tissue during healing (I. Magnusson, et al., "New Attachment Formations Following Controlled Tissue Regeneration Using Biodegradable Membranes", J. Periodontal January, 1988 pp. 1–6). Tests showed some new formation of cementum and bone. Reproductions of this material demonstrated poor surgical handling characteristics due to its thin friable construction and also proved to be difficult to suture because of its brittleness. This material makes no provision for tissue ingrowth on either of its surfaces.

Another material that is commercially available for use in guided tissue regeneration is VICRYL Periodontal Mesh available from Johnson & Johnson. The VICRYL Periodontal Mesh is comprised of woven fibers made from a bioabsorbable copolymer of about 90% glycolide and 10% lactide. Studies have shown that the VICRYL Periodontal Mesh has had some success as a barrier material that provides for tissue regeneration (Fleisher et al., "Regeneration of lost attachment apparatus in the dog using Vicryl Absorbable Mesh", International Journal of Periodontics and Restorative Dentistry 2/1988 pp 45–55). Difficulties with this conventional woven construction include its inferior ability to maintain space adjacent to the defect and its marginal effectiveness as a tissue barrier because of the inherent porosity of the woven structure. This material is a single layer material of woven construction that is intended to both promote tissue ingrowth and simultaneously serve as a tissue barrier. As these are somewhat contradictory objectives for a single layer material of woven construction having a degree of inherent porosity, ingrowth can only be made to occur at the expense of the barrier function. The effectiveness of this material is therefore a compromise between the material's ability to allow for tissue ingrowth and the requirement to simultaneously function as a tissue barrier.

There remains a need for a bioabsorbable material for use as an effective cell-barrier that allows for tissue attachment on at least one surface, adds to the stability of the healing wound through blood infiltration and coagulation into the material, substantially precludes passage of tissue cells through the material, possesses adequate rigidity to ensure preservation of the desired space proximal to the defect and has acceptable surgical handling properties and strength.

Bioabsorbable materials are herein defined as those materials of either synthetic or natural origin which when placed into a living body are degraded through either enzymatic, hydrolytic or other chemical reactions, into byproducts which are either integrated into or expelled from the body.

Cells and tissue are herein defined as mammalian cells and mammalian tissue.

SUMMARY OF THE INVENTION

This invention provides an implantable bioabsorbable article useful for the separation and regeneration of mammalian tissue, comprising a fibrous matrix affixed in laminar relationship to at least one side of a cell-barrier sheet material wherein the fibrous matrix is a porous material that allows the infiltration of blood clot and the ingrowth of tissue, and the cell-barrier sheet material substantially precludes the passage and further ingrowth of tissue. A preferred embodiment provides a fibrous matrix laminarly affixed to both sides of the cell-barrier sheet material. The invention may be made in either a flat planar form or alternatively in a tubular form for use in, for example, nerve repair and nerve guidance applications. Preferred bioabsorbable materials include polyglycolic acid fibers for the fibrous matrix and a copolymer of polylactic acid and polyglycolic acid for the cell-barrier sheet material.

A method for making the implantable bioabsorbable article of the present invention is also provided.

DETAILED DESCRIPTION OF THE INVENTION

Figure 1:
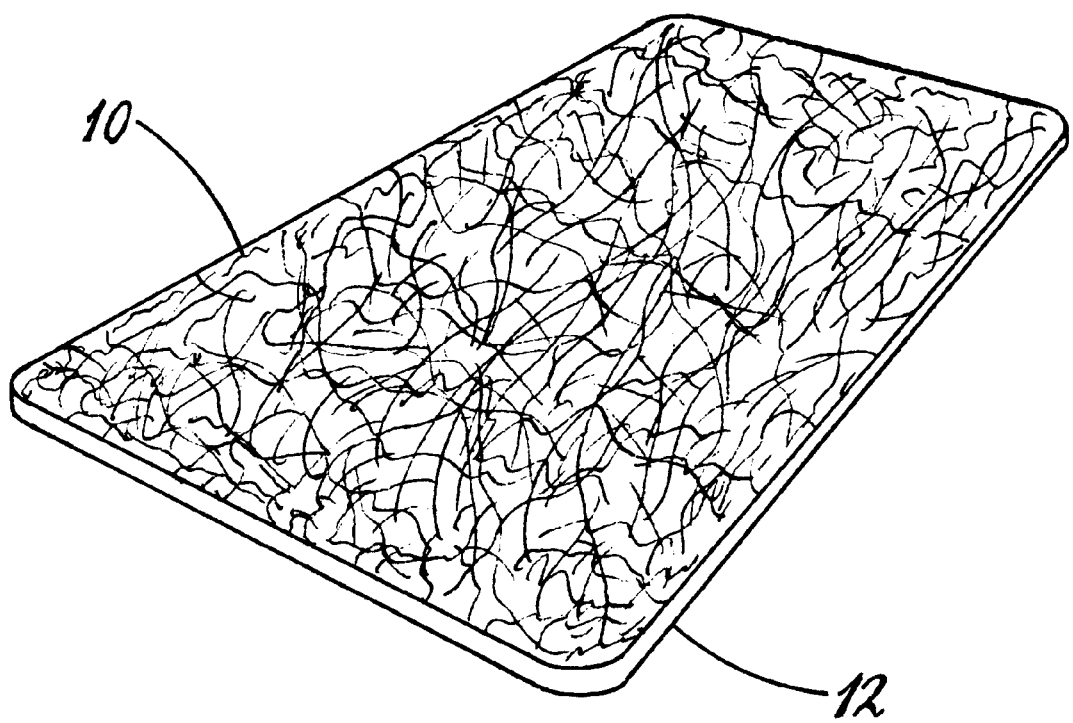
FIG. 1 is a perspective view of the implantable bioabsorbable article of the present invention having a fibrous matrix laminarly affixed to one side of a cell-barrier sheet material.

Reference will now be made in detail to the present invention, examples of which are illustrated in the drawings.

The basic structure of the article is shown in FIG. 1, comprising a composite material having a fibrous matrix 10 laminarly affixed to a cell-barrier sheet material 12. The fibrous matrix and cell-barrier sheet material are designed to be superimposed and affixed together in a laminar fashion so that the implantable bioabsorbable article has one surface that provides an open structure of void spaces capable of accommodating tissue ingrowth while the opposite surface provides a cell-barrier.

Figure 2A:
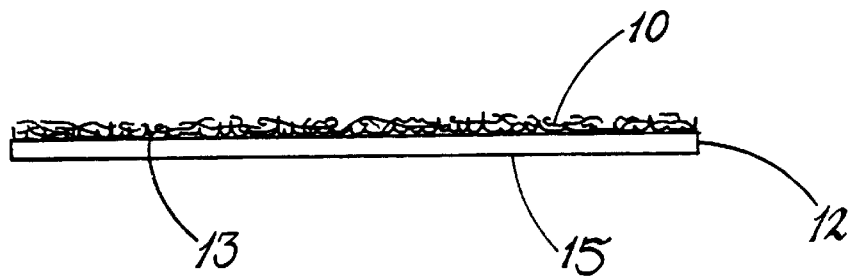
FIGS. 2A, 2B and 2C are cross sectional views of the implantable bioabsorbable article of FIG. 1 wherein the fibrous matrix is of unorganized configuration.

The cross section of FIG. 2A shows the implantable bioabsorbable article in further detail. The cell-barrier sheet material 12 has two opposing surfaces, designating the first opposing surface 13 and the second opposing surface 15. The fibrous matrix 10 is laminarly affixed to the first opposing surface 13 of the cell-barrier sheet material 12. By laminarly affixed is meant that the fibrous matrix 10 is attached directly to the surface of the cell-barrier sheet material 12 as shown by FIG. 2A, or extends through the first opposing surface 13 as shown by the cross section of FIG. 2B, or extends through the first surface 13 to the second surface 15 as shown by the cross section of FIG. 2C. Affixing is preferably accomplished by superimposing the fibrous matrix 10 on the first opposing surface 13 of the cell-barrier sheet material 12 while the cell-barrier sheet material 12 is in a softened or even liquid state as will be further described. Alternatively a bioabsorbable adhesive may be used to bond and thereby laminarly affix the fibrous matrix 10 to the first opposing surface 13 of the cell-barrier sheet material 12.

Figure 2B:
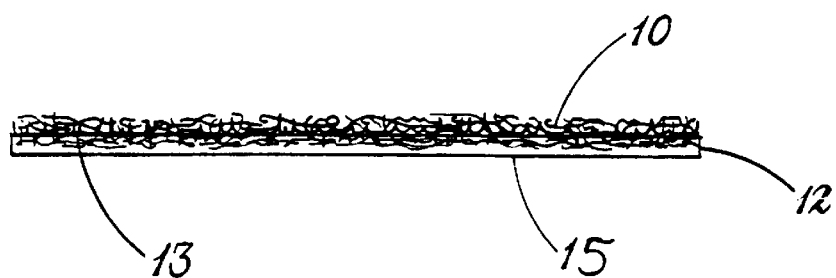
Figure 2C:
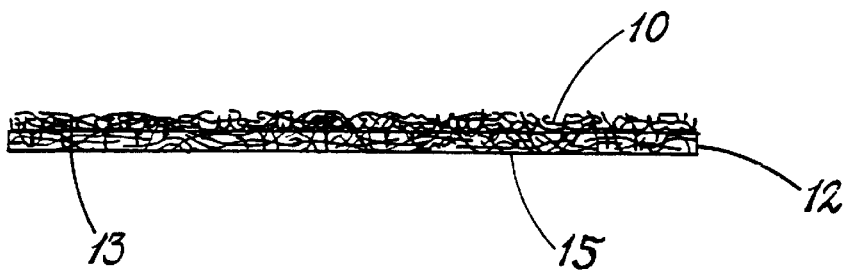
Figure 3:
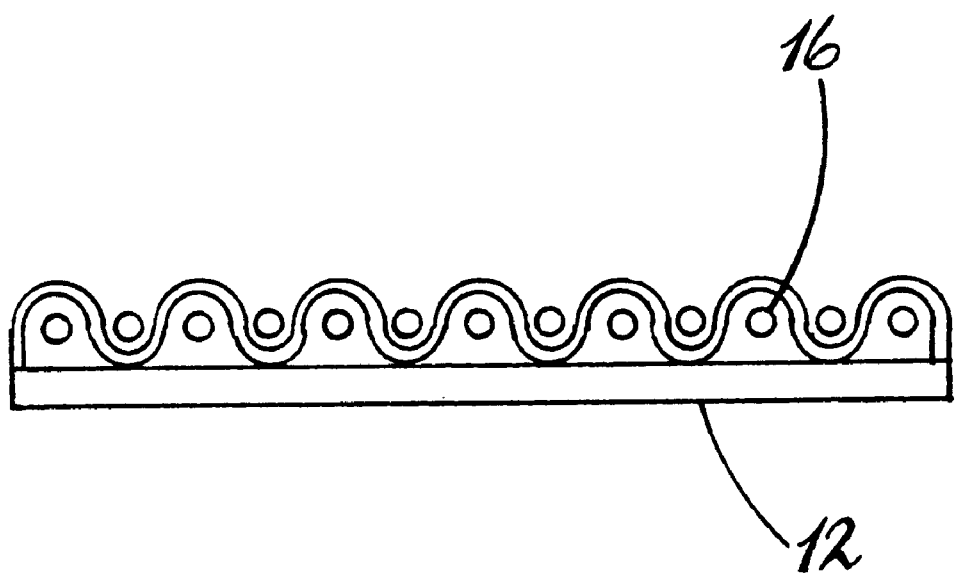
FIG. 3 is a cross sectional view of the implantable bioabsorbable article of FIG. 1 wherein the fibrous matrix is of organized configuration.

The fibrous matrix 10 comprises a mesh of fibers in either a random, unorganized configuration 14 as shown by the cross sections of FIGS. 2A, 2B and 2C, or alternatively the fibrous matrix comprises an organized fabric configuration 16 such as a fabric capable of supporting tissue ingrowth as shown by the cross section of FIG. 3. The organized configuration 16 is a fabric configuration which may be comprised of threads, yarns, nets, knits, weaves, laces, or felts of fibers. Alternatively, the fibrous matrix may be comprised of an open cell foam structure that will allow tissue ingrowth. Regardless of construction, the fibrous matrix must be sufficiently open to allow infiltration of blood and subsequent interconnection of ingrowing tissue through the open spaces existing between the fibers that comprise the matrix. In general, any bioabsorbable material having an open structure capable of tissue ingrowth may be suitable as the fibrous matrix so long as the mechanical properties and rate of bioabsorption are also appropriate for the intended application. The thickness of these fibrous matrix materials may vary depending on the end use application.

The cell-barrier sheet material is typically non-porous but may also be porous so long as the pore sizes are small enough to substantially preclude cell passage and ingrowth. Such a porous cell-barrier sheet material may be advantageous for certain applications, for example, where passage of nutrients or gasses across the material may be important.

The ability of an article to allow tissue ingrowth or conversely to substantially preclude cell passage and ingrowth can be determined by implanting the article into a dog and allowing time for healing to occur. The article and adjacent tissue complex should be harvested and histologically evaluated after three weeks, before substantial bioabsorption of the article has occurred. When evaluated, if mammalian cells, fibrous connective tissue cells or extracellular matrix, or collagen, have invaded the spaces between adjacent structures within the fibrous matrix, resulting in a connection between the article and adjacent tissue, the article is deemed capable of allowing tissue ingrowth and incapable of substantially precluding cell passage and ingrowth.

The cell-barrier sheet material should be composed of a synthetic bioabsorbable material such as, for example, polymeric materials including polycaprolactone, poly p-dioxanone, trimethylene carbonate, polyglycolic acid (PGA) or polylactic acid (PLA) or copolymers thereof. For periodontal applications, a preferred material is a copolymer of PLA and PGA, with preferred mixtures ranging from about 85% PLA and 15% PGA to about 50% PLA and 50% PGA. The equal ratio copolymer can be expected to bioabsorb at the fastest rate. For a comparison of bioabsorption rates of these materials, see Lewis, Danny H., Controlled Release of Bioactive Agents from Lactide/Glycolide Polymers, pp 1–41, *Biodegradable Polymers As Drug Delivery Systems*, Mark Chasin and Robert Langer (ed); Marcel Dekker, Inc., New York, N.Y., 1990.

Copolymers of PLA and PGA are polymerized from appropriate proportions of lactide and glycolide which are cyclic dimers based on lactic acid and glycolic acid respectively. The lactic acid components of the lactide dimer may be of either the d (dextrorotatory) or l (levorotatory) configuration or may be a mixture of the two configurational varieties (e.g., d,l lactide). Polymers containing mixtures of d,l lactides possess little or no polymeric crystallinity resulting in lessened rigidity and a relatively low glass transition temperature when compared with a more crystalline counterpart such as l lactide. The preferred periodontal repair embodiment for the cell-barrier sheet material component contains copolymers d,l lactide with glycolide which correspondingly provides minimal rigidity and a glass transition temperature conducive to subsequent thermal bonding of the embodiment incorporating a fibrous matrix on both sides of the barrier material.

These copolymers bioabsorb through hydrolysis returning them to their original components which are subsequently expelled from or assimilated into the body. The in vivo longevity of a particular copolymer is a function of its molecular weight combined with the ratio of its lactide and glycolide components. In general, the rate of hydrolysis is decreased with increasing lactic acid composition.

For periodontal applications, the fibers from which the fibrous matrix is constructed are preferably made of PGA in order to provide for bioabsorption of the matrix in a suitable time frame. Different fibers of the matrix may be comprised of different bioabsorbable polymers so that different fibers may be bioabsorbed at different rates.

The implantable bioabsorbable article should be mechanically capable of successfully retaining sutures for the amount of time required for enough healing to render the sutures unnecessary. The implantable bioabsorbable article should also be pliable and formable and not be brittle or thick so that it is hard to suture or difficult to conform to the ideal contours desired at the defect site. The article must not be so flexible that it collapses into the defect space but rather maintains and protects that space for an adequate time to allow healing to occur. These mechanical characteristics have been achieved with the implantable bioabsorbable article of the present invention and are the result of the structural combination of the fibrous matrix laminarly affixed to the cell-barrier sheet material.

Figure 4A:
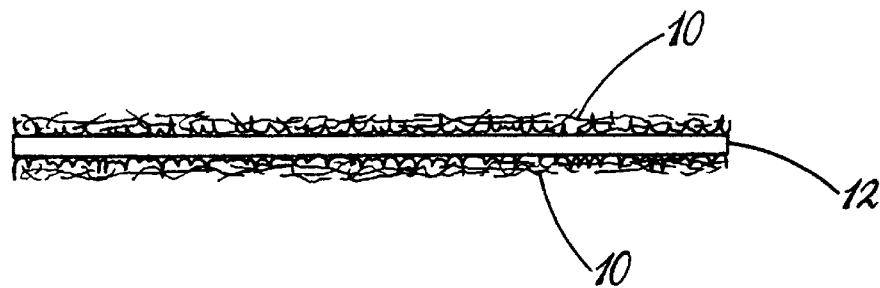
FIGS. 4A, 4B and 4C are cross sectional views of an alternative embodiment of the present invention having a fibrous matrix laminarly affixed to both sides of a cell-barrier sheet material.

The cross section of FIG. 4A describes a preferred alternative embodiment of the present invention wherein a fibrous matrix 10 is affixed to both opposing sides of a cell-barrier sheet material 12. As shown by the cross section of FIG. 4B, one way to produce this embodiment is to laminarly affix together the exposed cell-barrier surfaces of two samples 41 and 42 of the implantable bioabsorbable article having a fibrous matrix attached to only one side of the cell-barrier sheet material. The laminar juncture of the two samples 41 and 42 shown at.

Figure 4B:
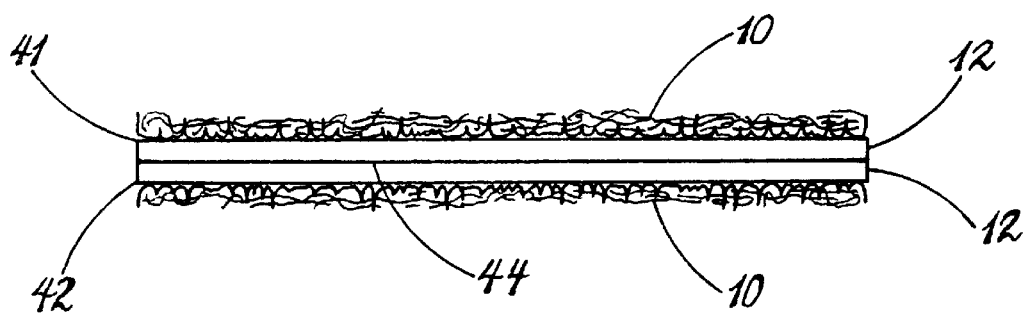
Figure 4C:
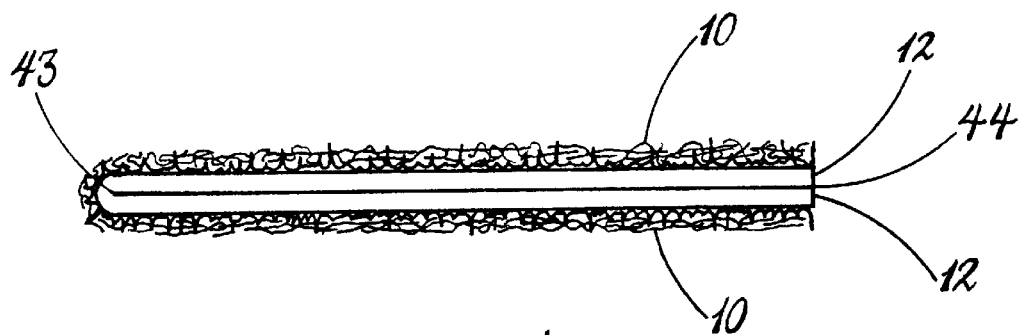

Alternatively, as shown by the cross section of FIG. 4C, it is possible to fold in half a single sample of the single-sided implantable bioabsorbable article with the surfaces of the cell-barrier material brought together and affixed. The fold is indicated at 43 and the laminarly affixed cell-barrier sheet material surface juncture is shown at 44. A method of affixing the cell-barrier sheet material surface will be described below.

Figure 5A:
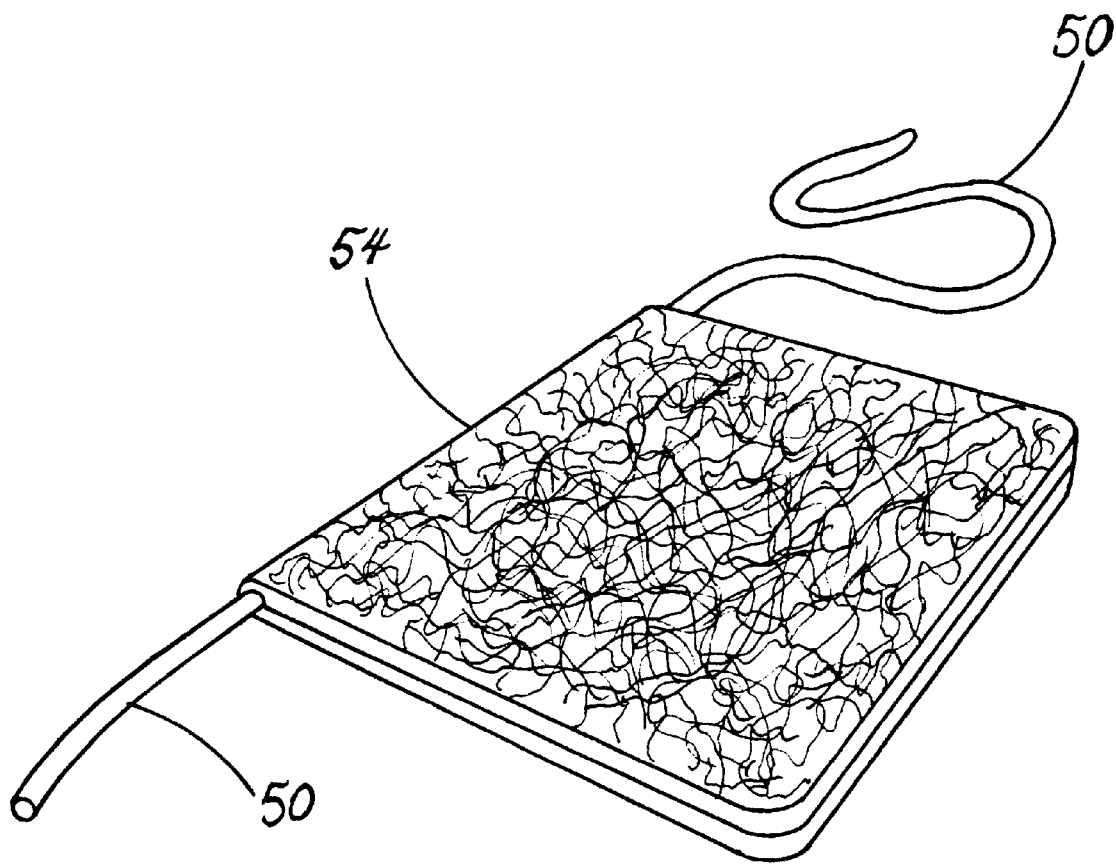
FIGS. 5A, 5B and 5C show the preferred periodontal repair embodiment of the present invention incorporating a bioabsorbable suture into its construction.
Figure 5B:
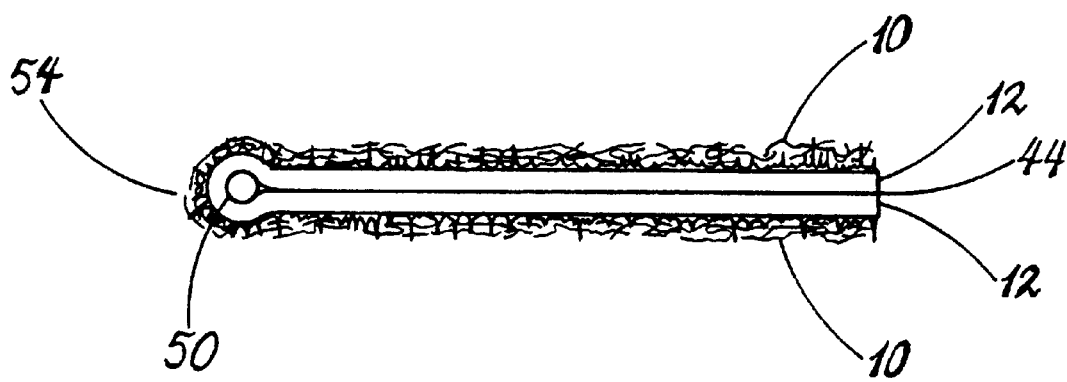
Figure 5C:
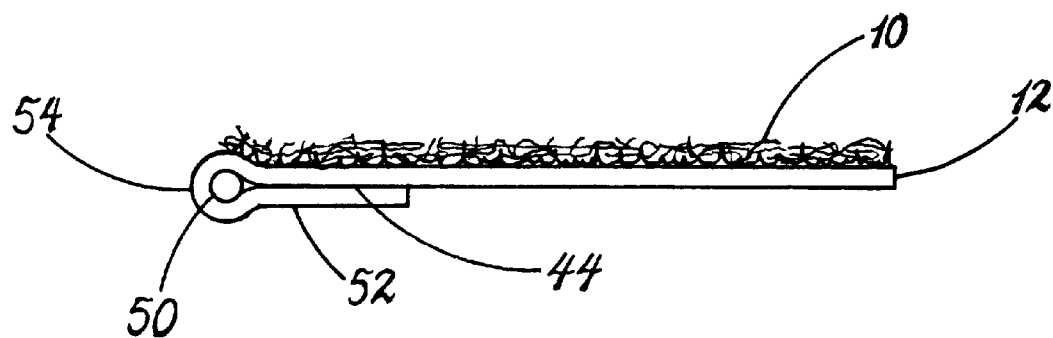

As shown by FIG. 5A, the implantable bioabsorbable article of the present invention may also be made so that it incorporates a bioabsorbable suture 50 to make the securing of the article to adjacent anatomical structures as simple as possible. This embodiment is considered to be at the present time the best mode of the present invention for periodontal repair. This embodiment is made most simply by placing a suture into the fold of the two-sided article described in FIG. 4C. The cross section of FIG. 5B shows this in detail. Other embodiments incorporating an affixed bioabsorbable suture are also possible. One such alternative embodiment is shown by FIG. 5C wherein a portion 52 of the cell-barrier material 12 is not covered by the fibrous matrix 10 and that portion 52 of the article is folded around a length of suture 50. The coronal edge of the article as implanted is indicated at 54. Other methods of attaching a suture may be used, for example, interweaving the suture through the thickness of the article.

In an alternative embodiment, the fibrous matrix, the fibers, the cell-barrier material, or any combination thereof may also be impregnated with any single or combination of substances such as antibiotics, antimicrobials, growth factors, differentiation factors, cell attachment factors or other such therapeutic agents. Impregnation of the implantable bioabsorbable article with such a therapeutic agent involves simply coating the article with the agent or alternatively incorporating the agent into the material from which either the fibrous matrix or the cell-barrier is constructed. For example, the therapeutic agent may be included in the polymer and solvent solution from which the cell-barrier is subsequently made. The incorporation of a therapeutic agent into the material of the implantable bioabsorbable article in this fashion would result in the release of the therapeutic agent into the living body in which the article is implanted. The presence of such an impregnating therapeutic agent in the implantable bioabsorbable article can be determined by accepted analytical techniques involving extraction, salvation, or other isolation methods whereby the therapeutic agent may be separated from the material from which the implantable bioabsorbable article is constructed.

Figure 6:
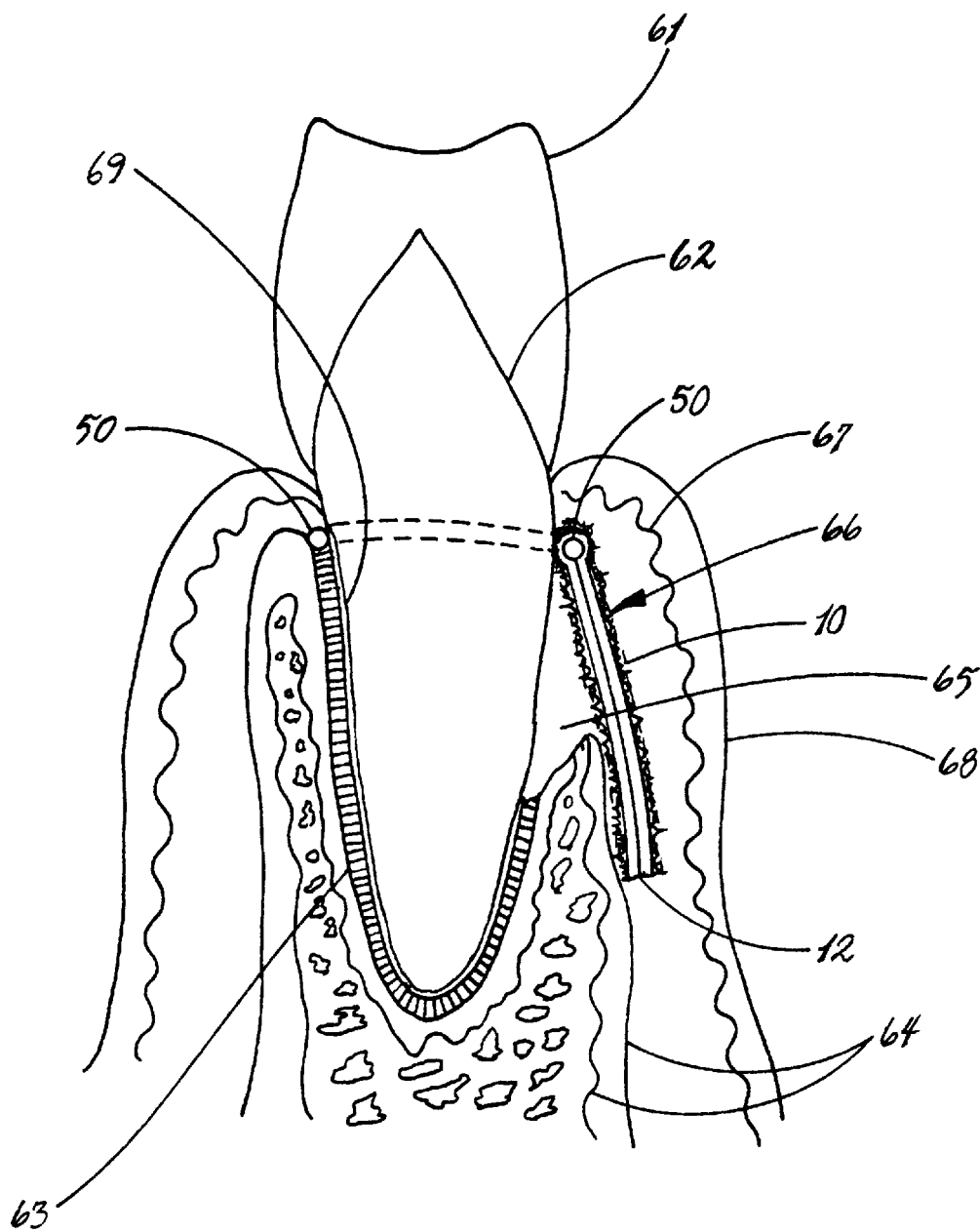
FIG. 6 is a cross section of a periodontal defect showing the preferred periodontal repair embodiment of the present invention.

A typical application of the implantable bioabsorbable article is shown in the cross section of FIG. 6. This figure illustrates the relationship of the implantable bioabsorbable article and adjacent anatomical structures immediately after the surgical placement of the article. The enamel tooth crown is indicated at 61 and the tooth root (dentin) is shown at 62. The periodontal ligament is indicated by 63, the supporting alveolar bone is shown by 64 and the cementum is shown at 69. A periodontal defect exists at 65 wherein the cementum, the periodontal ligament and alveolar bone are missing from the void space also shown by 65. This void space 65 will typically become filled with blood clot during or shortly after surgery. The implantable bioabsorbable article is shown in cross section at 66. In this particular case, the embodiment shown is the article having a fibrous matrix material 10 affixed to both sides of the cell-barrier material 12. The implantable bioabsorbable article 66 is shown serving as a barrier between the periodontal defect 65 and adjacent gingival connective tissue 67 and gingival epithelium 68. This embodiment of the implantable bioabsorbable article is shown with an incorporated bioabsorbable suture 50 as previously described in FIGS. 5A and 5B. The suture 50 is shown attaching the implantable bioabsorbable article to the tooth root 62 by encircling the tooth root 62.

According to the preferred method of making the implantable bioabsorbable article, the process of laminarly affixing the fibrous matrix to the cell-barrier sheet material is accomplished by placing a fibrous matrix into a bioabsorbable polymer and solvent solution and applying pressure and heat to evaporate the solvent, the bioabsorbable polymer forming the cell-barrier sheet material as the solvent evaporates. The selection of the solvent and the fibrous matrix material should be coordinated so that the fibrous matrix material is not readily soluble in the solvent. A preferred polymer and solvent solution is that of a PLA and PGA copolymer in a solvent such as acetone. The use of PGA fibers for the fibrous matrix is a preferred combination as such fibers are not readily soluble in the acetone.

Figure 7:
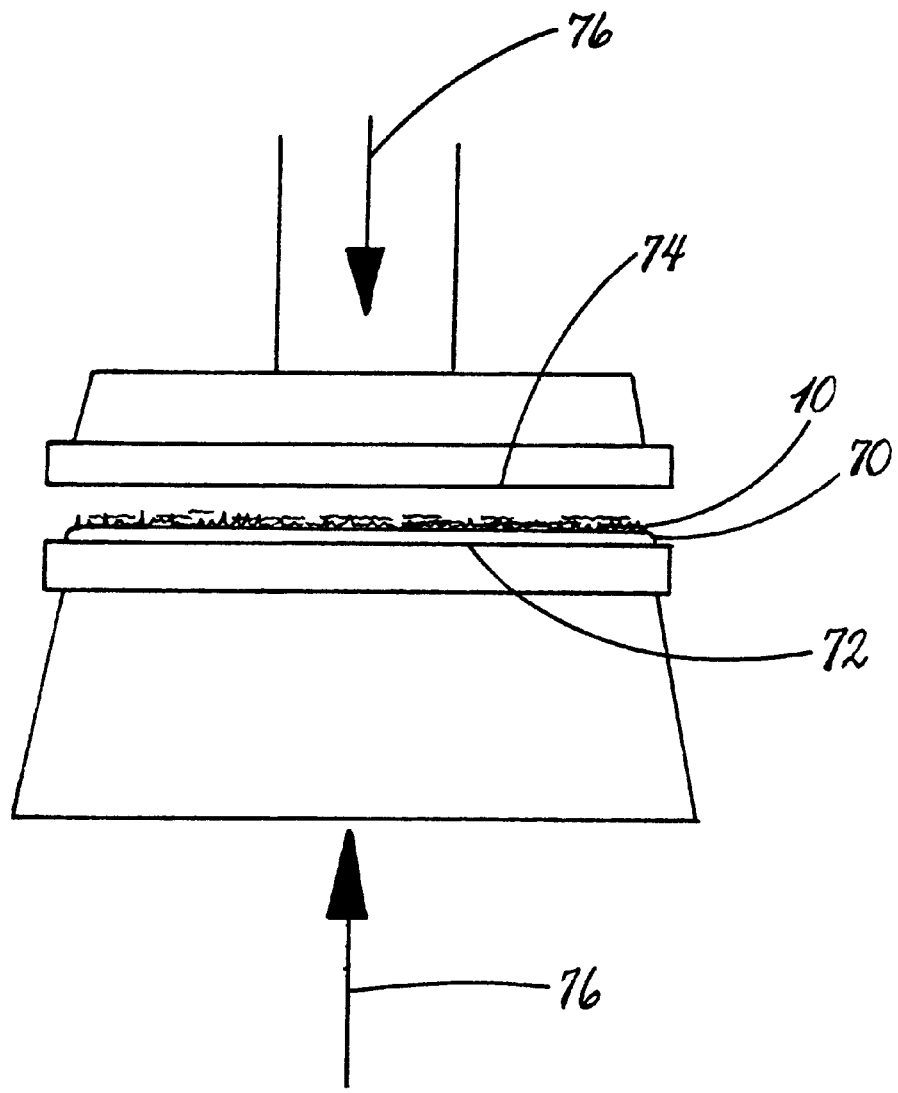
FIG. 7 shows a schematic drawing of the process of making the implantable bioabsorbable article of the present invention.

As shown by FIG. 7, the polymer and solvent solution 70 and fibrous matrix 10 are placed on a surface 72 capable of transferring heat at a temperature above the boiling point of the solvent in order to evaporate the solvent. The heating surface 72 must possess suitable release properties to allow removal of the finished implantable bioabsorbable article without damage. Suitable heating surface materials include polytetrafluoroethylene (PTFE), fluorinated ethylene-propylene (FEP), and other materials having adequate temperature capability and having release properties.

The preferred process for producing the implantable bioabsorbable article of the present invention is as follows. The fibrous matrix 10 and the solution of bioabsorbable polymer and solvent 70 are introduced between two opposing release surfaces 72 and 74 which are then compressed together as indicated by arrows 76 while heat in excess of the boiling temperature of the solvent is applied from release surface 72. The temperature should be higher than the boiling point of the solvent in order to assure rapid evaporation of the solvent within a few seconds. As a result of the rapid evaporation of the solvent, the fibrous matrix material is coated with the solvent carried polymer. Upon evaporation of the solvent, points of contact between adjacent fibers of the matrix are adhesively bonded. Simultaneously, the cell-barrier sheet material of the chosen bioabsorbable polymer or copolymer is deposited at the surface from which heat is applied. The resulting implantable bioabsorbable article is then removed from between the release surfaces.

Figure 8:
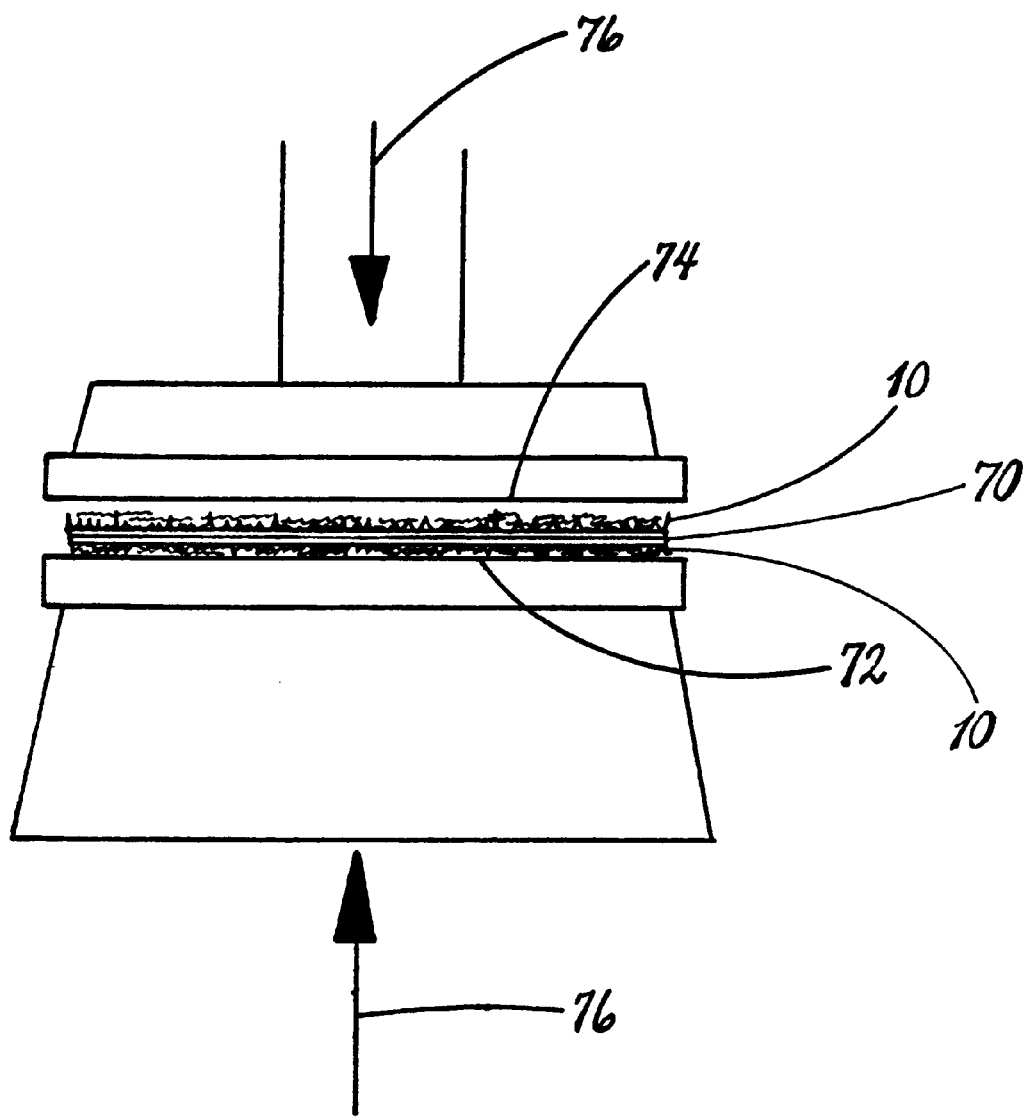
FIG. 8 shows a schematic drawing of a process of making the alternative embodiment having a fibrous matrix affixed to both sides of the cell-barrier sheet material.

To construct the two-sided embodiment shown by FIG. 4B having a fibrous matrix on two the opposing surfaces of the cell-barrier sheet material, two implantable bioabsorbable articles are prepared as described above. The two implantable bioabsorbable articles are placed so that their cell-barrier surfaces face each other and are superimposed on each other laminarly as shown by FIG. 8. Pressure and heat are applied at a temperature above the glass transition temperature of the barrier and below that of the fiber. This results in the two film surfaces adhering to one another to form a composite having a fibrous matrix on the two opposing surfaces of the cell-barrier sheet material. It is preferable to prepare the cell-barrier sheet materials with a PLA/PGA copolymer for the two-sided embodiment as the copolymer possesses a glass transition temperature between 40 and 60° C.

The embodiment incorporating a suture is made as described in the previous paragraph with the addition of a length of bioabsorbable suture placed between the two sheets of implantable bioabsorbable material before the two sheets are affixed together, the ends of the suture extending beyond the affixed sheets. Alternatively and preferably, as shown by the cross sections of FIGS. 5A, 5B and 5C, a single layer of the implantable bioabsorbable article is folded in half so that the suture is captured within the fold.

Figure 9:
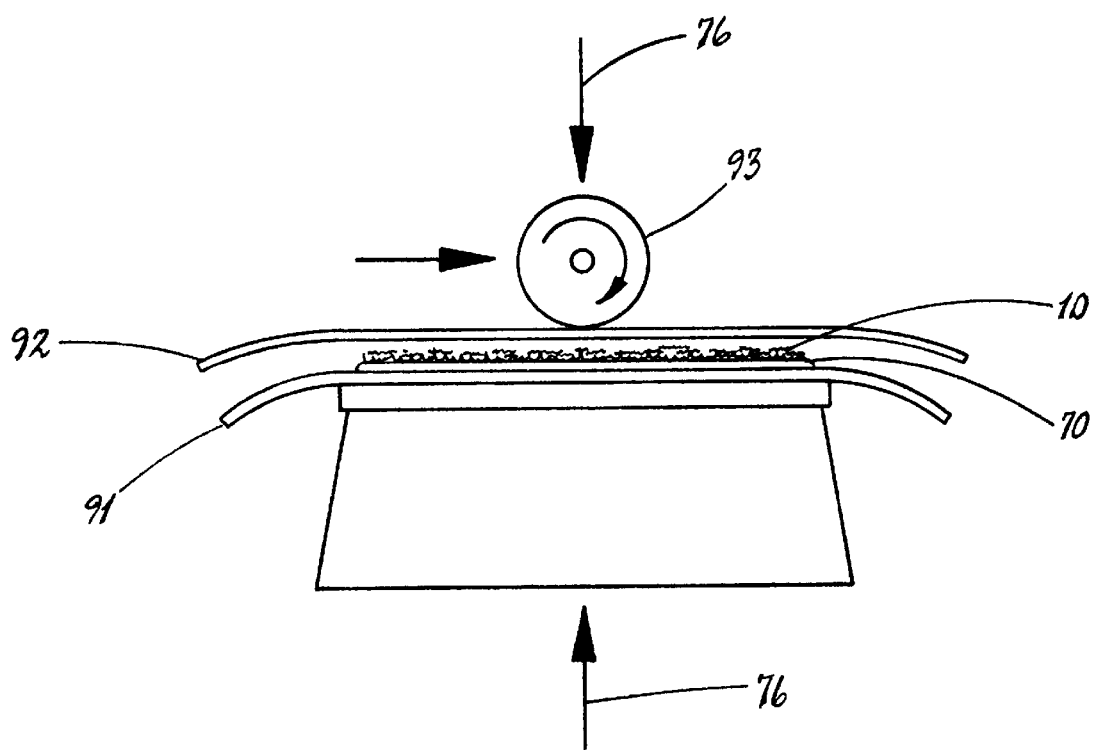
FIGS. 9 and 10 show a schematic drawings of two alternative processes of making the implantable material of the present invention.

FIG. 9 describes a preferred process wherein compression 76 is applied by a traversing roller 93 instead of a flat compression surface. The process is essentially the same as described previously. Separate removable upper and lower FEP film release layers 91 and 92 may be used optionally to provide the necessary release characteristics.

Figure 10:
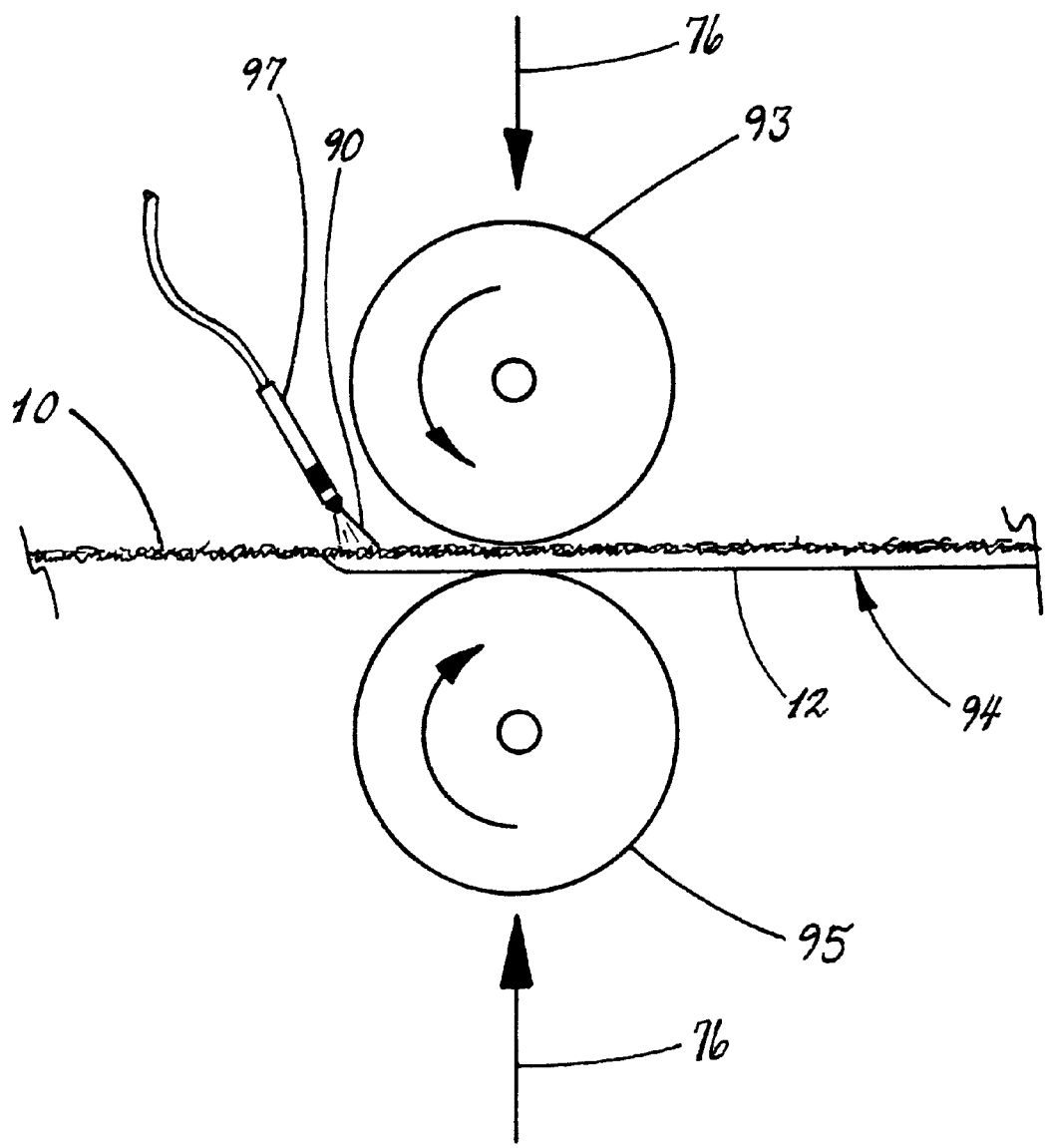

FIG. 10 describes an alternative process useful for a continuous process of manufacturing the implantable bioabsorbable article wherein the bioabsorbable polymer and solvent solution are applied as a liquid 90 to the fibrous matrix 10 from a liquid dispensing means 97. The fibrous matrix material 10 and applied bioabsorbable polymer solvent solution is fed between a heated roller 95 and an adjacent second roller 93. The finished implantable bioabsorbable article 94 emerges from between the two compressing rollers 95 and 93.

Figure 11:
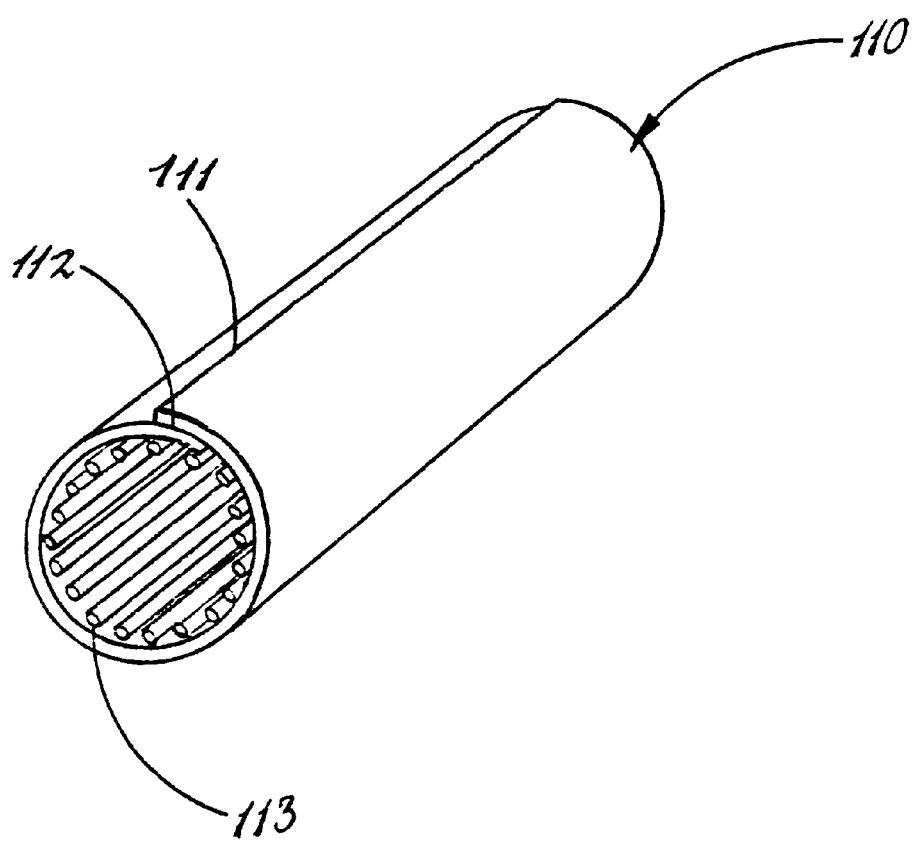
FIG. 11 shows the implantable bioabsorbable article of the present invention formed into a tube useful for repairs such as vascular and nerve guide repair.

As shown by FIG. 11, tubular constructions of the implantable bioabsorbable article are also possible. These are made by rolling the finished article, made as previously described, around a mandrel to form a tube 110, and applying heat and pressure to the overlapping edge III of the tubular article in order to seal the overlapping edge to the underlying material 112. Such a tubular article may have various implantable applications such as vascular repair and nerve repair. For nerve repair it is believed that excluding other tissues from the nerve repair site and constraining the healing nerve ends to prevent uncontrolled proliferation of nervous tissue are important factors in successful repair. It is also believed that retaining neurotropic and neurotrophic factors released by the distal nerve end, keeping these factors in the near vicinity of the proximal nerve end, is important in effecting successful nerve repair. The tubular article of the present invention is capable of providing for the exclusion of adjacent tissues from the nerve repair site, the containment of proliferating nervous tissue, and the retention of neurotropic and neurotrophic factors in the vicinity of the proximal nerve end. In a preferred embodiment for nerve repair, a tube is made by rolling the implantable bioabsorbable article into a tubular form as previously described with the fibrous matrix on the inner surface of the tube. It is preferred that the fibers be of an organized configuration in the form of parallel fibers on the inner surface of the tube oriented parallel to the longitudinal axis of the tube. It is believed that this fiber orientation provides a directional aid to the healing of the nerve between exposed nerve ends. The proximal and distal ends of a transected nerve will be placed in respective ends of this tubular article. These nerve ends may be abutted and sutured together, simply abutted, or left with a gap between the nerve ends when the tubular article is finally sutured or affixed by any suitable means to the nerve sheaths of the two nerve ends.

Figure 12:
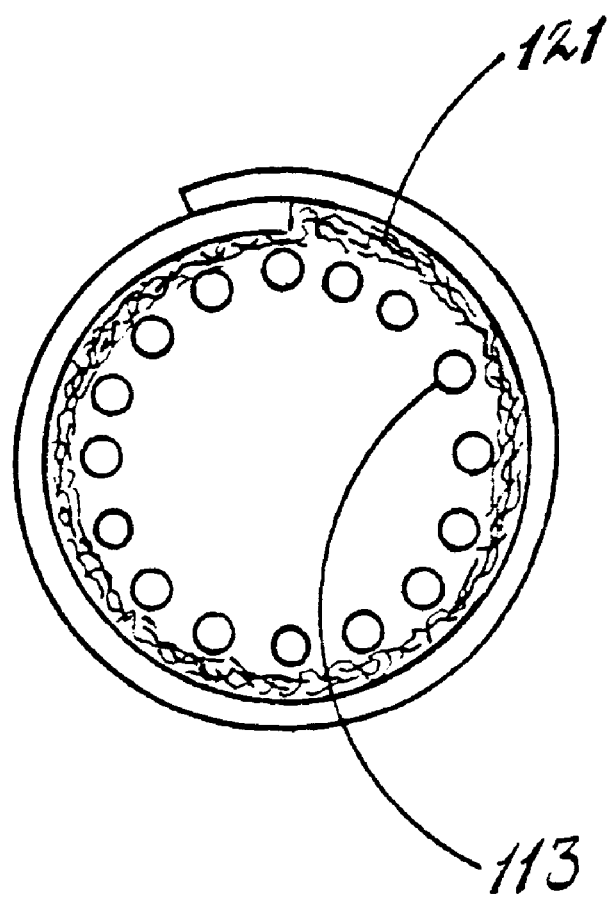
FIG. 12 shows a cross section of an alternative tubular embodiment.

As shown by the cross section of FIG. 12, an alternative tubular embodiment for nerve repair incorporates a layer of randomly configured fibrous matrix 121 between the outer cell-barrier sheet material surface of the tube and the inner surface of parallel longitudinally oriented fibers 113. This construction offers improved crush resistance. The longitudinally oriented fibers 113 are shown in exaggerated diameter for clarity.

In another tubular embodiment, an additional fibrous matrix may be used on the outer surface of the tube if attachment and stabilization of the surrounding external tissue is desired. A further embodiment may use a fibrous matrix outer tube surface with the cell-barrier sheet material forming the inner surface of the tube.

The implantable bioabsorbable article of the present invention may also be useful for repair of bone defects and bone regeneration. Specific applications include endochondral bone, intermembranous or round bone, and long bone. The implantable bioabsorbable article may include a fibrous matrix laminarly affixed to only one side of the cell-barrier sheet material or will preferably include having a fibrous matrix affixed to both sides of the cell-barrier sheet material. The article intended for bone repair should be sufficiently rigid to guarantee the maintenance of space adjacent to a bone defect.

The implantable bioabsorbable article of the present invention may also be useful in the prevention of soft tissue adhesions, particularly those of the peritoneum including pelvic adhesions. The preferable implantable bioabsorbable article may include a fibrous matrix laminarly affixed to only one side of the cell-barrier sheet material or optionally will include having a fibrous matrix affixed to both sides of the cell-barrier sheet material. The fibrous matrix is useful for stabilizing the implantable bioabsorbable article at the desired location to prevent the occurrence of an adhesion at that location. The fibrous matrix is effective to the extent that the implantable bioabsorbable article can simply be placed at the desired location without the necessity of further securing means.

EXAMPLE 1

Approximately 40 to 45 milligrams of individual 30 micron diameter polyglycolic acid (PGA) 1 to 2 inch long fibers were air laid in a random configuration on the surface of a stainless steel screen. The fibers were fabricated from PGA homopolymer with an average molecular weight in excess of 100,000 daltons.

A first sheet of 0.020 inch thick FEP clear film 91 as shown by FIG. 9, was placed onto a 4×4 inch horizontally oriented aluminum plate that had been heated to approximately 100° C. The fibrous matrix was removed from the stainless steel screen on which it had previously been fabricated, and was placed onto the first sheet of FEP film 91. Approximately 0.2 grams of 1:10 to 1:15 (w/w) solution of l-lactide polymer in methylene chloride (dichloromethane) solvent was poured onto the center of the fibrous matrix. A second sheet of FEP clear film 92 was laid over the top of the fiber matrix and polymer and solvent combination. The resulting sandwich was immediately compression-rolled between the aluminum plate and a rolling cylinder of about 3.5 inches length and 2 inch diameter. The roller effectively applied a force of approximately eight pounds across its width, as shown by arrow 76. Each compression roll process consisted of an approximately 3 inch pass of the roller across the surface of the fibrous matrix at a rate of approximately one complete cycle (2 passes) per second for a total of 2 minutes. The application of heat and pressure resulted in a finished implantable bioabsorbable article having a fibrous matrix laminarly affixed to one side of a cell-barrier sheet. Upon completion, the two FEP film sheets 91 and 92 and the finished implantable bioabsorbable article contained between the two FEP sheets was removed from the heated aluminum plate and allowed to cool under passive pressure applied by a 4"×4"×1" aluminum block.

After cooling, the two sheets of FEP were peelably removed from the finished implantable bioabsorbable article. The finished article was trimmed to 15 mm width and a 30 mm length. The article was folded in half across its 15 mm width with the cell-barrier surface on the inside. A 5-0 PGA suture obtained commercially was trimmed of its needle and placed into the fold of the material as shown by FIGS. 5A nad 5B. The folded article was placed between two FEP film sheets and compressed by the roller and heated plate apparatus described by FIG. 8. The plate temperature was 100° C. Pressure was again applied by traversing the roller back and forth over the article in one second cycles for a total period of 1 minute.

The finished implantable bioabsorbable article having an integrally attached suture was placed into a food grade pouch made of a polymer foil laminate. The pouch was sealed and gamma radiation sterilized at a total dosage of 2.0 Mrad.

EXAMPLE 2

The implantable bioabsorbable articles made and sterilized according to Example 1, each article incorporating an integrally attached suture as shown by FIGS. 5A and 5B, were implanted in dogs. The dog model has been used extensively for the testing of guided tissue regeneration techniques and materials (Caffesse et al. 1988, J. Periodontal Vol 59, 589–584; Claffey et al. 1989, J. Clin. Periodontal, Vol 16, 371–379).

At surgery, buccal and lingual full-thickness mucoperiosteal flaps were elevated from the first mandibular premolar to the mid portion of the mandibular first molar. Class II furcation defects were surgically created with high speed and hand instrumentation on the buccal aspects of the second and fourth mandibular premolars and the lingual aspects of the third mandibular premolars in four beagle dogs. The defects were created such that the roots were exposed between the mesial and distal line angles of the teeth and into but not through the furcation. The depth of the defects was approximately 4–6 millimeters. After the bone was removed, the exposed root surfaces were aggressively instrumented with high speed and hand instruments to remove any trace of the periodontal ligament and cementum. Reference notches were placed in the roots at the margins of the bony defects.

Defects were created in five separate mandibular premolar teeth per dog, the defects being intended to receive implantable bioabsorbable articles of the present invention. Each canine mandibular premolar tooth had two roots. The defects involved both roots of each of the five teeth for a total of ten roots potentially available for evaluation per dog. No sham operated controls were included in the experiment. It is well documented that surgical treatment of periodontal defect sites where no barrier material is placed will result in the formation of a long junctional epithelium and little or no regeneration of the periodontal attachment structures (Pfeifer et al., 1989, Int. J. Perio. Rest. Dent., Vol. 9, 263–273; Magnussen et al., 1988, J. Periodontal, Vol. 59, 1–6).

Each bioabsorbable article was first trimmed on the lateral and apical sides so that the material completely covered the defect and extended beyond the bony margins of the defect by at least 2 to 3 mm. The article was then positioned so that the coronal edge with the integrally attached suture was at the level of the cemento-enamel junction and completely covered the defect. The article was tied to the tooth with the integrally attached suture using a sling suture technique. The article was thus tightly adapted to the tooth surface along its coronal edge and draped over the surface of the bone. This created a protected space defined by the dimensions of the defect and the surface of the article which faced the defect. The muco-periosteal flaps were repositioned and the incisions closed using a combination of interrupted and vertical mattress sutures. Care was taken to make sure the membranes were completely covered by the soft tissue of the flaps.

The dogs received post operative oral hygiene care in the form of chlorhexidine (0.12%) flushes every other day starting seven days after surgery. Clinical parameters monitored during the healing period were gingival health, plaque index, exposure of material, gingival recession, and fragmentation or resorption of the exposed material.

Sacrifice times for the animals were 2, 4, 8 and 12 weeks postoperative. At the time of sacrifice, the experimental teeth were removed en bloc and placed in 70% ethanol/30% distilled water fixative. After fixation, the teeth were infiltrated and embedded in poly(methylmethacrylate) and fifteen 6–8 micron thick bucco-lingual sections spanning the mesio-distal width of each tooth were cut for histological evaluation with a Reichart-Jung Polycut S sledge microtome. One section representing the greatest length of each root and located as close to the furcation as feasible was chosen for evaluation. The parameters measured on each root available for evaluation were:

Apical Epithelial Migration (EM)—the distance from the apical extent of the epithelium to the gingival margin.

New Bone (NB)—the distance from the base of the instrumented root surface to the coronal extent of the new regenerated bone.

New Cementum (NC)—distance from the base of the instrumented root surface to the coronal extent of regenerated new cementum.

Defect Depth (DD)—the base of the instrumented root surface to the gingival margin (the area "at risk" for regeneration).

For EM, NB and NC, the distances were divided by DD and multiplied by 100 to obtain a percentage of the defect depth. The values for all available roots for each dog were averaged to obtain a single value for each dog. No adequate sections were obtained for three roots of the 4 week dog, 1 root of the 8 week dog and three roots of the 12 week dog.

Histological evaluation of the specimens revealed a mild chronic inflammatory response to the bioabsorbable membranes which was consistent with the response reported in the literature for this group of polymers (for example see Matlaga, B. F., and Salthouse, T. N., 1983; J. Biomed. Mat. Res. Vol. 19, 349–365). Fibrous connective tissue had infiltrated the fibrous matrix of the implantable bioabsorbable articles and there was clear interdigitation of collagen fibers between the ingrown tissue and the adjacent connective tissue of the flap. In all cases, the epithelium had migrated to a point at or very near the coronal border of the implantable bioabsorbable articles where the migration appeared to have been halted. In addition, at the two week time frame, the integrity of the implantable bioabsorbable article was substantially intact creating a barrier, as evidenced by a plane of separation between the flap tissue and the defect space. Also at the two week time frame the granulation tissue in the defect space had an immature appearance with a limited amount of extracellular matrix deposition and minimal differentiation of the tissue types.

At the remaining time frames, the integrity of the implantable bioabsorbable article was somewhat fragmented due to the resorption process. However, maturation of the tissues had occurred allowing measurement of the amount of newly regenerated bone and cementum. The resulting values are shown in Table I.

TABLE I

| 4 wk (N = 7) | 8 wk (N = 9) | 12 wk (N = 7) |
| --- | --- | --- |
| EM = 31% ± 10% | EM = 44% ± 13% | EM = 52% ± 22% |
| NB = 27% ± 13% | NB = 30% ± 13% | NB = 32% ± 18% |
| NC = 65% ± 15% | NC = 60% ± 11% | NC = 54% ± 17% |

Epithelial migration along the root surface can proceed at the rate of between 0.5 mm and 1.0 mm per day. If allowed to progress unimpeded, the epithelium would have migrated apically along either the outside of the implantable bioabsorbable articles or along the root surfaces. The data from this experiment show that the migration of the epithelium was limited by the fibrous connective tissue ingrowth and attachment to the implantable bioabsorbable articles. Concurrently, protection of the defect space from the epithelium and the gingival connective tissue by the implantable bioabsorbable articles allowed the regeneration of new bone in the defect space and new cementum on the root surfaces.

EXAMPLE 3

The preferred embodiment currently utilizes d,l PLA:PGA copolymer ratios between 50:50 and 85:15 for the cell-occlusive barrier forming material to provide a desirable in vivo bioabsorption rate for the periodontal application. Examples of the preferred embodiment were fabricated in accordance with the description of Example 1 with the following exceptions:

A. Approximately 38 to 42 milligrams of approximately 25 micrometer diameter PGA staple fibers were utilized in the fabrication of the fibrous matrix.

B. Individual samples were made utilizing d,l PLA:PGA copolymer ratios of either 85:15, 75:25, 60:40, and 50:50 for the cell-occlusive barrier forming material.

C. Each of the preferred embodiments utilizing d,l PLA:PGA copolymer ratios of either 85:15, 75:25, or 60:40 were fabricated with an approximately 1:3 to 1:5 (w/w) solution of the respective copolymer in acetone instead of in methylene chloride as described in Example 1.

EXAMPLE 4

A tubular article useful for tissue repair such as, for example, nerve repair, was constructed as follows.

A group of 1.5 inch long, 30 micron diameter PGA fibers were laid out approximately parallel in a strip about 0.5 inch wide, thus forming a fibrous matrix of organized configuration. 0.2 grams of about 1:5 (w/w) solution of 85:15 PLA:PGA copolymer in acetone was placed on this strip of fibers and heated and compressed in the apparatus of FIG. 8 in the same manner as described in Example 1. The resulting implantable bioabsorbable article having a fibrous matrix of approximately parallel fibers was then trimmed to a rectangular shape. The article was then wrapped around a 3.5 mm inch diameter mandrel to form a tube with the fibers on the inside of the resulting tube and with the fibers approximately parallel to the longitudinal axis of the tube. The exposed edge of the implantable bioabsorbable tube was sealed to the outer surface of the tube through compression at a temperature of about 100° C.

EXAMPLE 5

A second tubular article was made according to the description of Example 4 with the addition of a layer of 20 milligrams of individual 30 micron diameter PGA fibers arranged in a random configuration. The additional fiber was first placed onto the release surface and the strip of approximately parallel fibers then placed on top of the layer of randomly configured fibers, and the same copolymer and solvent solution of Example 4 was placed on the matrix. Compression and heat was applied with the apparatus of FIG. 9 in the same manner as described in FIG. 1. The resulting article was fashioned into a tube in the same manner as described in Example 4.

I claim:

1. A bioabsorbable article useful for the separation and regeneration of tissue comprising:
    a) a bioabsorbable, pliable, not brittle, cell-barrier polymeric sheet material being defined by a length, a width, and a thickness wherein the thickness has the smallest dimension, and wherein surfaces bounded by the length and width define first and second opposing surfaces, said first and second opposing surfaces being separated by the thickness of the sheet material;
    b) a bioabsorbable fibrous matrix laminarly affixed to the first opposing surface of said bioabsorbable cell-barrier sheet material to cover at least a portion of the first opposing surface; and
    c) a bioabsorbable fibrous matrix laminarly affixed to the second opposing surface of said bioabsorbable cell-barrier sheet material to cover at least a portion of the second opposing surface.

2. The article of claim 1 wherein both the cell-barrier sheet material and the fibrous matrix are comprised of a synthetic bioabsorbable material selected from the group consisting of polylactic acid, polyglycolic acid, poly-P-dioxanone, trimethylene carbonate, polycaprolactone and copolymers thereof.

3. The article of claim 2 wherein both the cell-barrier sheet material and the fibrous matrix are comprised of a copolymer of polylactic acid and polyglycolic acid.

4. The article of claim 2 wherein the cell-barrier sheet material is comprised of a copolymer of polylactic acid and polyglycolic acid and the fibrous matrix is comprised of polyglycolic acid fibers.

5. The article of claim 4 wherein the cell-barrier sheet material is comprised of a copolymer of about 50% polylactic acid and 50% polyglycolic acid.

6. The article of claim 4 wherein the cell-barrier sheet material is comprised of a copolymer of about 65% polylactic acid and 35% polyglycolic acid.

7. The article of claim 4 wherein the cell-barrier sheet material is comprised of a copolymer of about 85% polylactic acid and 15% polyglycolic acid.

8. The article of claim 1 wherein the fibrous matrix comprises a mesh of fibers in a random, unorganized configuration.

9. The article of claim 1 wherein the bioabsorbable fibrous matrix comprises a mesh of fibers in an organized configuration selected from the group consisting of threads, yarns, nets, knits, weaves, laces and felts.

10. The article of claim 1 wherein the cell-barrier sheet material is porous having a pore size small enough to substantially preclude the passage and ingrowth of tissue.

11. The article of claim 1 incorporating a suture affixed to the bioabsorbable article.

12. The article of claim 1 wherein at least a portion of the article is impregnated with a substance selected from the group consisting of antibiotics, antimicrobials, growth factors, differentiation factors and cell attachment factors.

13. A bioabsorbable article for promoting tissue regeneration, comprising a length of pliable, not brittle, bioabsorbable material having a first outer surface adapted for supporting tissue ingrowth, a second outer surface opposed to the first outer surface and adapted for supporting tissue ingrowth, the first and second outer surfaces each extending substantially the length of the bioabsorbable material, and a polymeric barrier between the first and second surfaces and extending substantially the length of the bioabsorbable material, the barrier adapted to substantially prevent tissue migration between the first and second outer surfaces.

14. The article of claim 13, wherein the length of bioabsorbable material is substantially planar in shape.

15. The article of claim 13, further comprising a suture attached to the length of bioabsorbable material.

16. A multi-layered bioabsorbable article for promoting tissue regeneration, comprising a pliable, not brittle, substantially cell-impermeable polymeric inner layer defined by a length, a width, and a thickness wherein the thickness has the smallest dimension, and wherein surfaces bounded by the length and width define first and second opposing surfaces, a first cell-permeable outer layer superposed on a first surface of the inner layer, and a second cell-permeable outer layer superposed on a second surface of the inner layer opposite the first surface so that the inner layer is positioned between and separates the first and second outer layers.

17. The article of claim 16, wherein the article is substantially planar in shape.

18. The article of claim 16, further comprising a suture attached to the article.

19. A bioabsorbable article useful for the separation and regeneration of tissue comprising:
    a) a bioabsorbable, pliable, not brittle, cell-barrier sheet material being defined by a length, a width, and a thickness wherein the thickness has the smallest dimension, and wherein surfaces bounded by the length and width define first and second opposing surfaces, said first opposing surface being in a first plane and said second opposing surface being in a second plane, said planes being separated by the thickness of the sheet material;
    b) a bioabsorbable fibrous matrix laminarly affixed to the first opposing surface of said bioabsorbable cell-barrier sheet material to cover at least a portion of the first opposing surface; and
    c) a bioabsorbable fibrous matrix laminarly affixed to the second opposing surface of said bioabsorbable cell-barrier sheet material to cover at least a portion of the second opposing surface.

20. A bioabsorbable article for promoting tissue regeneration, comprising a length of pliable, not brittle, bioabsorbable material having a first outer surface adapted for supporting tissue ingrowth, a second outer surface opposed to the first outer surface and adapted for supporting tissue ingrowth, the first and second outer surfaces each extending substantially the length of the bioabsorbable material, and a cell barrier between the first and second surfaces and extending substantially the length of the bioabsorbable material, the barrier adapted to substantially prevent tissue migration between the first and second outer surfaces.

21. A multi-layered bioabsorbable article for promoting tissue regeneration, comprising a pliable, not brittle, substantially cell-impermeable inner layer defined by a length, a width, and a thickness wherein the thickness has the smallest dimension, and wherein surfaces bounded by the length and width define first and second opposing surfaces, a first cell-permeable outer layer superposed on a first surface of the inner layer, and a second cell-permeable outer layer superposed on a second surface of the inner layer opposite the first surface so that the inner layer is positioned between and separates the first and second outer layers.

* * * * *